United States Patent [19]

Ng et al.

[11] Patent Number: 5,481,020

[45] Date of Patent: Jan. 2, 1996

[54] OPIATE RECEPTOR LIGANDS

[75] Inventors: Simon Ng, Walnut Creek; Robert L. Warne, San Francisco; Ronald N. Zuckermann, Berkeley; Eric J. Martin, El Cerrito; Reyna J. Simon, Felton, all of Calif.

[73] Assignee: Chiron Corporation, Emeryville, Calif.

[21] Appl. No.: 366,830

[22] Filed: Dec. 30, 1994

[51] Int. Cl.$^6$ .................................................. C07C 271/10
[52] U.S. Cl. ........................................... 560/27; 560/28
[58] Field of Search ......................................... 560/27, 28

[56] References Cited

U.S. PATENT DOCUMENTS

| | | | |
|---|---|---|---|
| 5,223,535 | 6/1993 | Hansen et al. | 514/489 |
| 5,246,959 | 9/1993 | Hansen et al. | 514/400 |
| 5,272,175 | 12/1993 | Hansen et al. | 514/487 |
| 5,364,850 | 11/1994 | Hansen et al. | 514/255 |

*Primary Examiner*—José G. Dees
*Assistant Examiner*—Joseph M. Conrad, III
*Attorney, Agent, or Firm*—Grant D. Green; Robert P. Blackburn

[57] ABSTRACT

Compounds of Formula 1 bind opioid receptors: which binds to the opioid receptor:

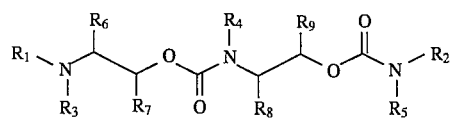

6 Claims, No Drawings

OPIATE RECEPTOR LIGANDS

DESCRIPTION

Technical Field

The invention relates generally to the field of medicinal chemistry, and specifically to compounds which bind to opioid receptors.

Background of the Invention

Opioid receptors are named for their binding affinity to morphine and other opium-derived compounds. The three classes of opioid receptor are designated μ (morphine-like), κ(ketazocine-like), and δ.

Morphine:

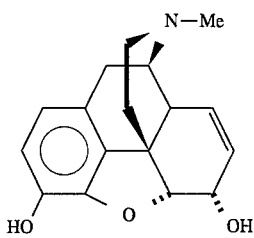

Ketazocine:

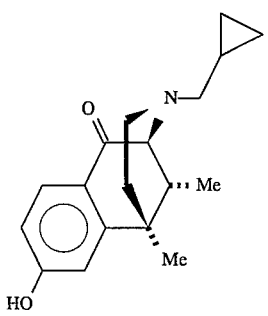

Disclosure of the Invention

One aspect of the invention is a compound of Formula 1 which binds to the opioid receptor:

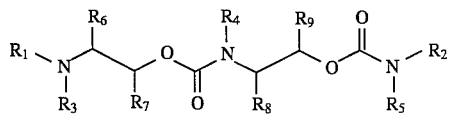

wherein $R_1$ is a group of the formula

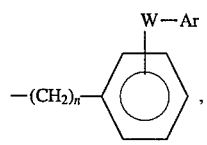

where W is —$(CH_2)_a$— (where a is 0, 1, or 2), —O—, —NH—, —S—, —SO—, or —$SO_2$—, and Ar is phenyl, phenyl-alkyl, phenyl substituted with 1–3 halo, nitro, lower alkyl, hydroxy, amino, alkylamino, dialkylamino, and/or hydroxy-lower alkyl groups, and n is 0, 1, 2, 3, or 4;

$R_2$ and $R_3$ are each independently H, lower alkyl, or

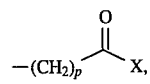

where X is H, OH, lower alkyl, or lower alkoxy, and p is 0, 1, 2, or 3;

$R_4$ is

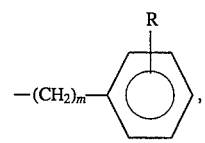

where m is 0, 1, 2, or 3, and R is 1–3 halo, nitro, lower alkyl, hydroxy, amino, alkylamino, dialkylamino, and/or hydroxy-lower alkyl groups;

$R_5$ is cycloalkyl, bicycloalkyl, or tricycloalkyl;

$R_6$, $R_7$, $R_8$, and $R_9$ are each independently H or lower alkyl.

Another aspect of the invention is the method of modulating opioid receptor activity, comprising contacting an opioid receptor with a compound of formula 1.

Modes of Carrying out the Invention

A. Definitions

The term "compound of formula 1" refers to compounds of the formula:

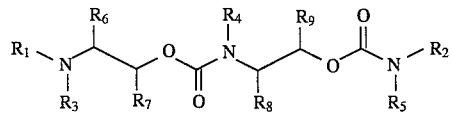

wherein $R_1$ is a group of the formula

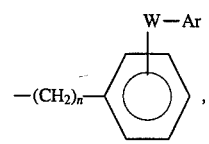

where W is —$(CH_2)_a$— (where a is 0, 1, or 2), —O—, —NH—, —S—, —SO—, or —$SO_2$—, and Ar is phenyl, phenyl-alkyl, phenyl substituted with 1–3 halo, nitro, lower alkyl, hydroxy, amino, alkylamino, dialkylamino, and/or hydroxy-lower alkyl groups, and n is 0, 1, 2, 3, or 4;

$R_2$ and $R_3$ are each independently H, lower alkyl, or

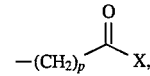

where X is H, OH, lower alkyl, or lower alkoxy, and p is 0, 1, 2, or 3;

$R_4$ is

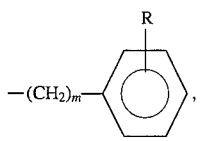

where m is 0, 1, 2, or 3, and R is 1–3 halo, nitro, lower alkyl, hydroxy, amino, alkylamino, dialkylamino, and/or hydroxy-lower alkyl groups;

$R_5$ is cycloalkyl, bicycloalkyl, or tricycloalkyl; and $R_6$, $R_7$, $R_8$, and $R_9$ are each independently H or lower alkyl, and pharmaceutically acceptable salts and esters thereof. In a presently preferred class of compounds, $R_3$, $R_6$, $R_7$, $R_8$, and $R_9$ are all H. In a presently preferred subclass of the invention, $R_1$ is 2-(2-hydroxymethylphenylthio)benzyl, and $R_4$ is 4-hydroxybenzyl. Preferably, $R_5$ is norbornyl or bicyclooctyl, most preferably norbornyl.

The term "alkyl" as used herein refers to saturated hydrocarbon radicals containing from 1 to 30 carbon atoms, inclusive. Alkyl radicals may be straight, branched, or cyclic. Exemplary alkyl radicals include n-pentyl, n-hexyl, n-octyl, n-dodecyl, 2-dodecyl, 4-octadecyl, 3,5-diethylcyclohexyl, duryl, and the like. The term "lower alkyl" as used herein refers to straight, branched, and cyclic chain hydrocarbon radicals having from 1 to 8 carbon atoms, such as methyl, ethyl, propyl, isopropyl, n-butyl, s-butyl, t-butyl, n-pentyl, n-hexyl, cyclopentyl, cyclohexyl, 2-methylcyclopentyl, cyclopentylacetyl, and the like. "Alkoxy" refers to radicals of the formula —OR, where R is alkyl as defined above: "lower alkoxy" refers to alkoxy radicals wherein R is lower alkyl. "Hydroxy-lower alkyl" refers to radicals of the formula HO—R—, where R is lower alkylene of 1 to 8 carbons, and may be straight, branched, or cyclic. "Hydroxy-lower alkoxy" refers to radicals of the formula HO—R—O—, where R is lower alkylene of 1 to 8 carbons, and may be straight, branched, or cyclic. "Lower alkoxy-lower alkyl" refers to groups of the formula $R_a$O—$R_b$—, where $R_a$ and $R_b$ are each independently lower alkyl. "Lower alkoxy-lower alkoxy" refers to groups of the formula $R_a$O—$R_b$O—, where $R_a$ and $R_b$ are each independently lower alkyl.

"Alkenyl" refers to hydrocarbon radicals of 2–20 carbon atoms having one or more double bonds. Alkenyl radicals may be straight, branched, or cyclic. Exemplary alkenyl radicals include 1-pentenyl, 3-hexenyl, 1,4-octadienyl, 3,5-diethylcyclohexenyl, and the like. "Lower alkenyl" refers to alkenyl radicals having 2–8 carbon atoms.

The term "alkynyl" refers to hydrocarbon radicals of 2–20 carbon atoms having one or more triple bonds. Alkynyl radicals may be straight, branched, or cyclic. Exemplary alkynyl radicals include 1-pentynyl, 3-hexynyl, octa-2-yn-6-enyl, 3,5-diethylcyclohexynyl, and the like. "Lower alkynyl" refers to alkynyl radicals having 2–8 carbon atoms.

The term "cycloalkyl" refers to alkyl radicals of 3–20 carbon atoms having at least one ring of carbon atoms. "Bicycloalkyl" refers to alkyl radicals of 7–20 carbon atoms having at least two fused rings of carbon atoms (in which one or more carbon atoms are members of both rings). "Tricycloalkyl" refers to alkyl radicals of 7–20 carbon atoms having at least three fused rings of carbon atoms (in which one or more carbon atoms of each ring are simultaneously members of another ring).

The term "haloalkyl" refers to an alkyl radical substituted with one or more halogen atoms. Exemplary haloalkyl radicals include trifluoromethyl, 2,2,2-trifluoroethyl, 3-chlorocyclohexyl, 2-bromo-3-chlorocyclohexyl, 2,3-dibromobutyl, and the like.

The term "haloalkenyl" refers to an alkenyl radical substituted with one or more halogen atoms. Exemplary haloalkenyl radicals include 3-chloroprop-2-enyl, 4,4-dichlorobut-2-enyl, 5-bromo-3-methylcyclohex-2-enyl, and the like.

"Aryl" refers to aromatic hydrocarbons having up to 14 carbon atoms, preferably phenyl or naphthyl. "Aryl-lower alkyl" refers to radicals of the form Ar—R—, where Ar is aryl and R is lower alkyl. "Aryloxy" refers to radicals of the form Ar—O—, where Ar is aryl. "Aryloxy-lower alkyl" refers to radicals of the form ArO—R—, where Ar is aryl and R is lower alkyl.

The term "acyl" refers to a radical of the formula RCO—, in which R is H, alkyl as defined above, phenyl, benzyl or naphthyl. Exemplary acyl groups include acetyl, propionyl, formyl, t-butoxycarbonyl, benzoyl, and the like. "Lower acyl" refers to radicals wherein R is lower alkyl.

The term "halo" refers to a halogen radical, such as F, Cl, Br, or I.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of opiate addiction in a patient may be reduction of opiate effect (blockade), or the prevention of relapse in a patient who has been cured.

The term "preparation" refers to a sample to be tested for the presence of opioid receptor. Preparations may be whole tissues, tissue homogenates, host cells (e.g., recombinant host cells), biopsy samples, blood and/or blood fractions, lymph, and the like.

B. General Method

Compounds of the invention are easily synthesized by standard chemical methods. The presently-preferred method of synthesis is the "submonomer" technique described by P. Bartlett et al., WO91/19735, incorporated herein by reference. Briefly, a suitable side chain is coupled to an amino alcohol (e.g., ethanolamine), typically by displacing a leaving group on the side chain by the amino alcohol nitrogen. The product is protected, and reacted with phosgene to form an intermediate of Formula 2:

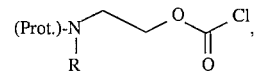

where R is the side chain, and Prot. indicates a protecting group. This intermediate is then coupled to a suitable activated solid-phase synthesis resin, and the protecting group removed. The terminal nitrogen may then be acylated by another intermediate of Formula 2. Alternatively, one may employ the procedures disclosed in WO94/06451, incorporated herein by reference.

The reactants employed in synthesis of the compounds are generally commercially available. Other reactants (e.g., less-common substituted amines) may be prepared by standard chemical means from amines that are commercially available.

Compounds of the invention may be assayed for activity using standard protocols. For example, one may employ the protocol demonstrated in the Examples below to determine binding of compounds of the invention to any desired receptor subtype (e.g., using different sources of tissue). Compounds which exhibit strong binding to receptors will exert either agonistic or (more usually) antagonistic activity, which may be determined by means of appropriate tissuebased or in vivo assays known in the art. Compounds within the scope of the invention may easily be assayed for activity by standard receptor-binding assays.

The compounds of The invention may be administered by a variety of methods, such as intravenously, orally, intramuscularly, intraperitoneally, bronchially, intranasally, and so forth. The preferred route of administration will depend upon the nature of the compound and the condition to be treated. Compounds may be administered orally if well absorbed and not substantially degraded upon ingestion (compounds of the invention are generally resistant to proteases). The compounds may be administered as pharmaceutical compositions in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, sustained-release patches, and the like. Alternatively, one may incorporate or encapsulate the compound in a suitable polymer matrix or membrane, thus providing a sustained-release delivery device suitable for implantation near the site to be treated locally. Other devices include indwelling catheters and devices such as the Alzet® minipump. Further, one may provide the compound in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

Compounds of the invention may be used to detect the presence of opiate receptor in tissues, cells, body fluids, and the like, exploiting the fact that compounds of the invention bind to opiate receptor. In general, a sample is obtained, and is contacted with a compound of the invention under physiological conditions. The sample is then rinsed, and examined for binding of the compound. Examination may be facilitated by using labeled compound (e.g., radiolabeled with $^3$H, $^{13}$C, $^{125}$I, and the like). This assay may be useful, inter alia, for examining expression of opiate receptor in recombinant host cells, and for studying pathological distributions of opiate receptor.

C. Examples

The examples presented below are provided as a further guide to the practitioner of ordinary skill in the art, and are not to be construed as limiting the invention in any way.

EXAMPLE 1

(Preparation of Compounds)

Compounds of the invention are prepared as follows:
A.) Preparation of CHIR 6028

1.) Loading Bromoacetic acid on Wang resin

Wang resin (2.71 g, 1.98 mmole) with substitution 0.73 mmole/g was swollen with 15 ml dichloromethane (DCM) in a 50 ml reaction vessel and was drained later. Bromoacetic acid (1.12 g, 8 mmole) was mixed with 1 M DCC/NMP (8 ml, 8 mmole) and 10 ml DCM. Dimethyl-aminopyridine (58.5 mg, 0.48 mmole) was added into the resin. 18 ml of activated Bromoacetic acid/DCC/NMP/DCM solution was then added into the reaction vessel. The resin mixture was shaken for 60 min at room temperature and then was drained and washed with 15 ml DCM 3×, 15 ml DMF 2× and 15 ml IPA. The loaded resin (1) was dried under vacuo to provide bromoacetyl.

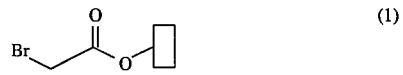

2.) Coupling loaded Wang resin with 2-Aminonorbornane

Loaded resin (200 mg, 100 μmole)(1) was swollen with 2 ml DMSO in a 8 ml reaction vessel, and then drained. 2-Aminonorbornane (593 μl, 5 mmole) was mixed with DMSO (1.907 ml) to prepare a 2.5 ml solution of 2 M 2-aminonorbornane/DMSO which was then added to the reaction vessel. The resin mixture was shaken at 45° C. for 4 hr. It was drained and then washed with 3 ml DMF 6× and 3 ml DCM 6× to provide the loaded resin (2) N-norbornylaminoacetyl.

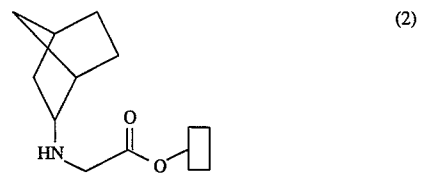

3.) Acylating resin with Bromoethylchloroformate (BECF)

The loaded resin (2) was swollen with 3 ml DCM in a 8 ml reaction vessel and then drained. BECF (84 μl, 750 μmole) was mixed with DIEA (128 μl, 750 μmole) and DCM (2.2 ml) to prepare a 2.5 ml of 0.3 M BECF/DIEA/DCM solution which was then added into the reaction vessel. The resin mixture was shaken for 20 min at room temperature and then drained and washed with 3 ml DCM. The resin sample was treated with 2.5 ml of 0.3 M BECF/DIEA/DCM solution for 20 min again. It was drained and then washed with 3 ml DCM 6× and 3 ml DMF 6× to provide the loaded resin (3) N-(2-bromoethoxycarbonyl)-N-(2-norbornyl)aminoacetyl.

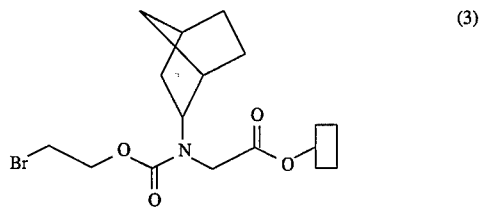

4.) Coupling resin with Tyramine

The loaded resin (3) was swollen with 2 ml DMSO in a 8 ml reaction vessel and then drained. Tyramine (2.2 ml, 2.5 mmole) was dissolved in DMSO (2.5 ml) to prepare a 2.5 ml of 1 M tyramine/DMSO solution which was then added into the reaction vessel. The resin mixture was shaken at 45° C. for 4 hr. It was then drained and washed with 3 ml DMF 6× and 3 ml DCM 6× to provide the loaded resin (4) N-(4-hydroxybenzyl-aminoethoxycarbonyl)-N-(2-norbornyl)aminoacetyl.

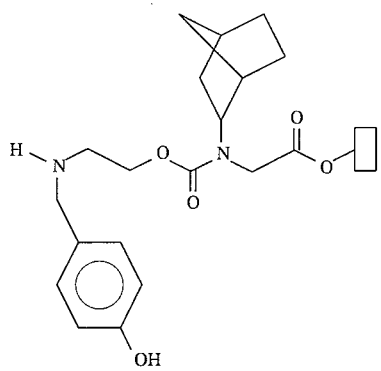

(4)

5.) Acylating resin with Bromoethylchloroformate (BECF)

All loaded resin (4) was swollen with 3 ml DCM in a 8 ml reaction vessel and then drained. BECF (84 µl, 750 µmole) was mixed with DIEA (128 µl, 750 µmole) and DCM (2.2 m) to prepare a 2.5 ml of 0.3 M BECF/DIEA/DCM solution which was then added into the reaction vessel. The resin mixture was shaken for 20 min at room temperature and then drained and washed with 3 ml DCM. The resin sample was treated with 2.5 ml of 0.3 M BECF/DIEA/DCM solution for 20 min again. It was drained and then washed with 3 ml DCM 6× and 3 ml DMF 6× to provide the loaded resin (5) N-(N'-(2 -bromoethoxycarbonyl)-N'-(4-hydroxybenzyl-aminoethoxycarbonyl)-N-(2-norbornyl)aminoacetyl.

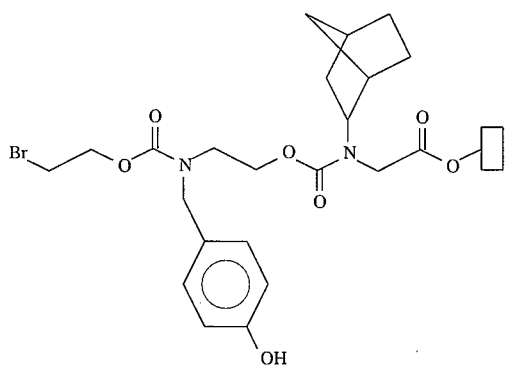

(5)

6.) Coupling resin with 2,2-Aminomethylphenoxybenzyl Alcohol

The loaded resin (5) was swollen with 2 ml DMSO in a 8 ml reaction vessel and then drained. 2,2-Aminomethylphenoxybenzyl alcohol (1.22 g, 10 mmole) was dissolved in DMSO (2.5 ml) to prepare a 2.5 ml of 2 M 2,2-aminomethylphenyl thiobenzyl alcohol/DMSO solution which was then added into the reaction vessel. The resin mixture was shaken at 45° C. for 4 hr. It was then drained and washed with 3 ml DMF 6× and 3 ml DCM 6X to provide the loaded resin (6), which was dried under vacuo to provide N-(N'-(2-(2-(2-hydroxymethylphenoxy)benzyl)aminoethoxycarbonyl)-N'-(4 -hydroxybenzyl-aminoethoxycarbonyl)-N-(2-norbornyl)aminoacetyl.

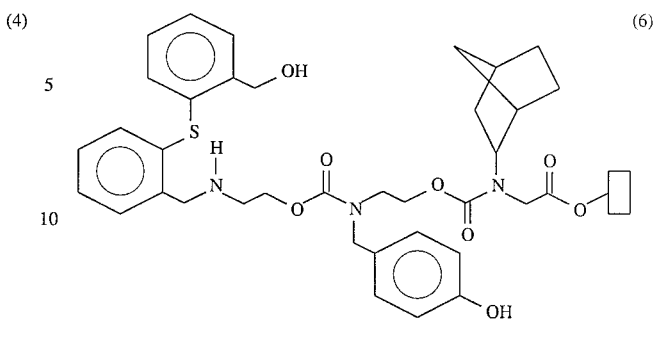

(6)

7.) Cleaving resin product

The dried resin (6) was put in a 8 ml reaction vessel. 3 ml of 90% trifluoroacetic acid/water was added into the reaction vessel. The carbamate resin was cleaved in TFA for 40 min at room temperature and then filtered into a 50 ml collection tube. All filtrate was concentrated to dryness under vacuo to give an oily crude product (7) N-(N'-(2-(2-(2 -hydroxymethylphenoxy)benzyl)aminoethoxycarbonyl)-N'-(4 -hydroxybenzylaminoethoxy-carbonyl)-N-(2-norbornyl)aminoacetic acid (46.2 mg, 67 µmole).

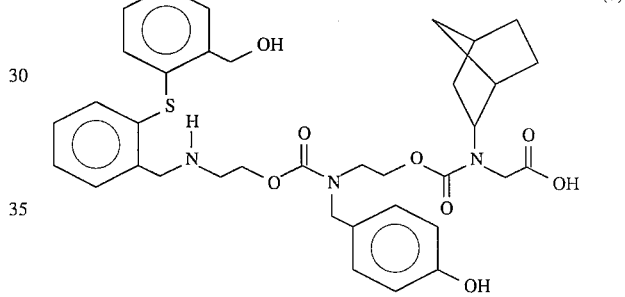

(7)

8.) Reversed-phase HPLC purification

The crude product (7) was dissolved in 30% methanol/H$_2$O (5 ml) and loaded onto a C18 RP-HPLC column (Vydac, 22×250 mm). A 10 ml/min flow rate and a linear gradient of 5–55% buffer B in 50 min were used. The product ($R_t$ 40.8 min) was then lyophilized to give (5.6 mg, 12% yield) of product as an oil. Mass spectrometry (MH+ expected 692.29, found 692.36).

B.) Preparation of other compounds

1.) Similarly, proceeding as in part A) above, but substituting adamantylamine, bicyclooctylamine for norbornylamine in step 2.), the following compounds are prepared:
N-(N'-(2-(2-(2-hydroxymethylphenoxy)benzyl)aminoethoxycarbonyl)-N'-(4 -hydroxybenzylaminoethoxy-carbonyl)-N-(2-adamantyl)aminoacetic acid; and
N-(N'-(2-(2-(2-hydroxymethylphenoxy)benzyl)aminoethoxycarbonyl)-N'-(4 -hydroxybenzylaminoethoxy-carbonyl)-N-(2-bicyclooctyl)aminoacetic acid.

2.) Proceeding as in part A) and B)(1) above, but substituting 2-bromopropylchloroformate for bromoethylchloroformate in step 3), the following compounds are prepared:
N-(N'-(2-(2-(2-hydroxymethylphenoxy)benzyl)aminoethoxycarbonyl)-N'-(2 -(4-hydroxybenzylamino)propoxy-carbonyl)-N-(2-norbornyl)aminoacetic acid;
N-(N'-(2-(2-(2-hydroxymethylphenoxy)benzyl)aminoethoxycarbonyl)-N'-(2-(4 -hydroxybenzylamino)propoxy-carbonyl)-N-(2-adamantyl)aminoacetic acid; and N-(N'-(2-(2-(2-hydroxymethylphenoxy)benzyl)aminoethoxycarbonyl)-N'-(2-(4-hydroxybenzylamino)propoxy-carbonyl)-N-(2-bicyclooctyl)aminoacetic acid.

3.) Proceeding as in part A) and B)(1–2) above, but substituting 3-hydroxybenzylamine, 2-hydroxybenzylamine, 4-hydroxyphenethylamine, 3-hydroxyphenethylamine, 2-hydroxyphenethylamine, 4-(dimethylamino)benzylamine, 4-nitrophenethylamine, 4-nitrobenzylamine, 4-chlorobenzylamine, and 4-hydroxymethylbenzylamine for tyramine in step 4), the following compounds are prepared:

N-(N'-(2-(2-(2-hydroxymethylphenoxy)benzyl)aminoethoxycarbonyl)-N'-(2-(3-hydroxybenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxybenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxybenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxybenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxybenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxybenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxyphenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxyphenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-hydroxyphenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(3-hydroxyphenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxyphenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxyphenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxyphenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxyphenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxyphenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-dimethylaminobenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-dimethylaminobenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-dimethylaminobenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrophenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrophenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrophenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrobenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrobenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrobenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-chlorobenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-chlorobenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-chlorobenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxymethylbenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxymethylbenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-hydroxymethylbenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(3-hydroxybenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxybenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxybenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxybenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxybenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxybenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxyphenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxyphenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-hydroxyphenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(3-hydroxyphenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxyphenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxyphenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxyphenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxyphenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxyphenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-dimethylaminobenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-dimethylaminobenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-dimethylaminobenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrophenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrophenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrophenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrobenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrobenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrobenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-chlorobenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-chlorobenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-chlorobenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxymethylbenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxymethylbenzylamino)propoxycarbonyl)-N-(2-adamantyl)aminoacetic acid; and N-(N'-(2-(2-(2-hydroxymethylphenoxy)benzyl)aminoethoxycarbonyl)-N'-(2-(4-hydroxymethylbenzylamino)propoxycarbonyl)-N-(2-bicyclooctyl)aminoacetic acid.

4.) Proceeding as in part A) and B)(1–3) above, but substituting 2-(3-hydroxymethylphenoxy)benzylamine, 2-(2-hydroxyethylphenoxy)benzylamine, 2-(2-hydroxymethylphenoxy)phenethylamine, 2-(2-hydroxymethylphenoxy)benzylamine, 2-(2hydroxymethylphenylamino)benzylamine, for 2-(2-hydroxymethylphenoxy)benzylamine in part 6), 'the following compounds are prepared:

N-(N'-(2-(2-(3-hydroxymethylphenylamino)benzyl)aminoethoxycarbonyl)-N'-(2-(3-hydroxybenzylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(3-hydroxybenzylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(3-hydroxybenzylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(2-hydroxybenzylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(2-hydroxybenzylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(2-hydroxybenzylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-hydroxyphenethylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(4-hydroxyphenethylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(4-hydroxyphenethylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(3-hydroxyphenethylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(3-hydroxyphenethylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(3-hydroxyphenethylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(2-hydroxyphenethylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(2-hydroxyphenethylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(2-hydroxyphenethylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-dimethylaminobenzylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(4-dimethylaminobenzylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(4-dimethylaminobenzylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-nitrophenethylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(4-nitrophenethylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(4-nitrophenethylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-nitrobenzylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(4-nitrobenzylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(4-nitrobenzylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-chlorobenzylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(4-chlorobenzylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(4-chlorobenzylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-hydroxymethylbenzylamino)ethoxycarbonyl)-N-(2-norbornyl)aminoacetic acid;

N-(N'-(2-(2-(3-hydroxymethylphenylthio)benzyl)aminoethoxycarbonyl)-N'-(2-(4-hydroxymethylbenzylamino)ethoxycarbonyl)-N-(2-adamantyl)aminoacetic acid;

N-(N'-(2-(2-(3-hydroxymethylphenylthio)benzyl)aminoethoxycarbonyl)-N'-(2-(4-hydroxymethylbenzylamino)ethoxycarbonyl)-N-(2-bicyclooctyl)aminoacetic acid;

N-(N'-(2-(2-(3-hydroxymethylphenylthio)benzyl)aminoethoxycarbonyl)-N'-(2-(3-hydroxybenzylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(3-hydroxybenzylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(3-hydroxybenzylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(2-hydroxybenzylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(2-hydroxybenzylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(2-hydroxybenzylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-hydroxyphenethylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(4-hydroxyphenethylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(4-hydroxyphenethylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(3-hydroxyphenethylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(3-hydroxyphenethylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(3-hydroxyphenethylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(2-hydroxyphenethylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(2-hydroxyphenethylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(2-hydroxyphenethylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-dimethylaminobenzylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(4-dimethylaminobenzylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(4-dimethylaminobenzylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-nitrophenethylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(4-nitrophenethylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(4-nitrophenethylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-nitrobenzylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(4-nitrobenzylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(4-nitrobenzylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-chlorobenzylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(4-chlorobenzylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(4-chlorobenzylamino)propoxycarbonyl)-N-(2-bicyclooctyl)aminoacetic acid;

N-(N'-(2-(2-(3-hydroxymethylphenylthio)benzyl)aminoethoxycarbonyl)-N'-(2-(4-hydroxymethylbenzylamino)propoxycarbonyl)-N-(2-norbornyl)aminoacetic acid;

N-(N'-(2-(2-(3-hydroxymethylphenylthio)benzyl)aminoethoxycarbonyl)-N'-(2-(4-hydroxymethylbenzylamino)propoxycarbonyl)-N-(2-adamantyl)aminoacetic acid;

N-(N'-(2-(2-(3-hydroxymethylphenylthio)benzyl)aminoethoxycarbonyl)-N'-(2-(4-hydroxymethylbenzylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(3-hydroxybenzylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(3-hydroxybenzylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(3-hydroxybenzylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(2-hydroxybenzylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(2-hydroxybenzylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(2-hydroxybenzylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-hydroxyphenethylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(4-hydroxyphenethylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(4-hydroxyphenethylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(3-hydroxyphenethylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(3-hydroxyphenethylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(3-hydroxyphenethylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(2-hydroxyphenethylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(2-hydroxyphenethylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(2-hydroxyphenethylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-dimethylaminobenzylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(4-dimethylaminobenzylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(4-dimethylaminobenzylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-nitrophenethylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(4-nitrophenethylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(4-nitrophenethylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-nitrobenzylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(4-nitrobenzylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(4-nitrobenzylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-chlorobenzylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(4-chlorobenzylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(4-chlorobenzylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-hydroxymethylbenzylamino)ethoxycarbonyl)-N-(2-norbornyl)aminoacetic acid;

N-(N'-(2-(2-(2-hydroxyethylphenylthio)benzyl)aminoethoxycarbonyl)-N'-(2-(4-hydroxymethylbenzylamino)ethoxycarbonyl)-N-(2-adamantyl)aminoacetic acid;

N-(N'-(2-(2-(2-hydroxyethylphenylthio)benzyl)aminoethoxycarbonyl)-N'-(2-(4-hydroxymethylbenzylamino)ethoxycarbonyl)-N-(2-bicyclooctyl)aminoacetic acid;

N-(N'-(2-(2-(2-hydroxyethylphenylthio)benzyl)aminoethoxycarbonyl)-N'-(2-(3-hydroxybenzylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(3-hydroxybenzylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(3-hydroxybenzylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(2-hydroxybenzylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(2-hydroxybenzylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(2-hydroxybenzylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-hydroxyphenethylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(4-hydroxyphenethylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(4-hydroxyphenethylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(3-hydroxyphenethylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(3-hydroxyphenethylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(3-hydroxyphenethylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(2-hydroxyphenethylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(2-hydroxyphenethylamino)propoxycarbonyl)-N-(2-adamantyl)aminoacetic acid;

N-(N'-(2(2-(2-hydroxyethylphenylthio)benzyl)aminoethoxycarbonyl)-N'-(2(2-hydroxyphenethylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-dimethylaminobenzylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(4-dimethylaminobenzylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(4-dimethylaminobenzylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-nitrophenethylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(4-nitrophenethylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(4-nitrophenethylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-nitrobenzylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(4-nitrobenzylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(4-nitrobenzylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-chlorobenzylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(4-chlorobenzylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(4-chlorobenzylamino)propoxycarbonyl)-N-(2-bicyclooctyl)aminoacetic acid;

N-(N'-(2-(2-(2-hydroxyethylphenylthio)benzyl)aminoethoxycarbonyl)-N'-(2-(4-hydroxymethylbenzylamino)propoxycarbonyl)-N-(2-norbornyl)aminoacetic acid;

N-(N'-(2-(2-(2-hydroxyethylphenylthio)benzyl)aminoethoxycarbonyl)-N'-(2-(4-hydroxymethylbenzylamino)propoxycarbonyl)-N-(2-adamantyl)aminoacetic acid;

N-(N'-(2-(2-(2-hydroxyethylphenylthio)benzyl)aminoethoxycarbonyl)-N'-(2-(4-hydroxymethylbenzylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(3-hydroxybenzylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(3-hydroxybenzylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(3-hydroxybenzylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(2-hydroxybenzylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(2-hydroxybenzylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(2-hydroxybenzylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-hydroxyphenethylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(4-hydroxyphenethylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(4-hydroxyphenethylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(3hydroxyphenethylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(3-hydroxyphenethylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(3-hydroxyphenethylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(2-hydroxyphenethylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(2-hydroxyphenethylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(2-hydroxyphenethylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-dimethylaminobenzylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(4-dimethylaminobenzylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(4-dimethylaminobenzylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-nitrophenethylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(4-nitrophenethylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(4-nitrophenethylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-nitrobenzylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(4-nitrobenzylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(4-nitrobenzylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-chlorobenzylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(4-chlorobenzylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(4-chlorobenzylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-hydroxymethylbenzylamino)ethoxycarbonyl)-N-(2-norbornyl)aminoacetic acid;

N-(N'-(2-(2-(2-hydroxymethylphenylthio)phenethyl)aminoethoxycarbonyl)-N'-(2-(4-hydroxymethylbenzylamino)ethoxycarbonyl)-N-(2-adamantyl)aminoacetic acid;

N-(N'-(2-(2-(2-hydroxymethylphenylthio)phenethyl)aminoethoxycarbonyl)-N'-(2-(4-hydroxymethylbenzylamino)ethoxycarbonyl)-N-(2-bicyclooctyl)aminoacetic acid;

N-(N'-(2-(2-(2-hydroxymethylphenylthio)phenethyl)aminoethoxycarbonyl)-N'-(2-(3-hydroxybenzylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(3-hydroxybenzylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(3-hydroxybenzylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(2-hydroxybenzylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(2-hydroxybenzylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(2-hydroxybenzylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-hydroxyphenethylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(4-hydroxyphenethylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(4-hydroxyphenethylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(3-hydroxyphenethylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(3-hydroxyphenethylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(3-hydroxyphenethylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(2-hydroxyphenethylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(2-hydroxyphenethylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(2-hydroxyphenethylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-dimethylaminobenzylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(4-dimethylaminobenzylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(4-dimethylaminobenzylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-nitrophenethylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(4-nitrophenethylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(4-nitrophenethylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-nitrobenzylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(4-nitrobenzylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(4-nitrobenzylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-chlorobenzylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(4-chlorobenzylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(4-chlorobenzylamino)propoxycarbonyl)-N-(2-bicyclooctyl)aminoacetic acid;

N-(N'-(2-(2-(2-hydroxymethylphenylthio)phenethyl)aminoethoxycarbonyl)-N'-(2-(4-hydroxymethylbenzylamino)propoxycarbonyl)-N-(2-norbornyl)aminoacetic acid;

N-(N'-(2-(2-(2-hydroxymethylphenylthio)phenethyl)aminoethoxycarbonyl)-N'-(2-(4-hydroxymethylbenzylamino)propoxycarbonyl)-N-(2-adamantyl)aminoacetic acid;

N-(N'-(2-(2-(2-hydroxymethylphenylthio)phenethyl)aminoethoxycarbonyl)-N'-(2-(4-hydroxymethylbenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(3-hydroxybenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxybenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxybenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxybenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxybenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxybenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxyphenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxyphenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-hydroxyphenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(3-hydroxyphenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxyphenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxyphenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxyphenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxyphenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxyphenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-dimethylaminobenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-dimethylaminobenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-dimethylaminobenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrophenethylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrophenethylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrophenethylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrobenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrobenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrobenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-chlorobenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-chlorobenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-chlorobenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxymethylbenzylamino)ethoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxymethylbenzylamino)ethoxycarbonyl)-N-(2-adamantyl)aminoacetic acid;

N-(N'-(2-(2-(2-hydroxymethylphenoxy)benzyl)aminoethoxycarbonyl)-N'-(2-(4-hydroxymethylbenzylamino)ethoxycarbonyl)-N-(2-bicyclooctyl)aminoacetic acid;

N-(N'-(2-(2-(2-hydroxymethylphenoxy)benzyl)aminoethoxycarbonyl)-N'-(2-(3-hydroxybenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxybenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxybenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxybenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxybenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxybenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxyphenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxyphenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-hydroxyphenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(3-hydroxyphenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(3-hydroxyphenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(3-hydroxyphenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(2-hydroxyphenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(2-hydroxyphenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(2-hydroxyphenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-dimethylaminobenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-dimethylaminobenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-dimethyaminobenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrophenethylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrophenethylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrophenethylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-nitrobenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-nitrobenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-nitrobenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-chlorobenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-chlorobenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-chlorobenzylamino)propoxycarbonyl)-N-(2-bicyclooctyl)aminoacetic acid;

N-(N'-(2-(2-(2-hydroxymethylphenoxy)benzyl)aminoethoxycarbonyl)-N'-(2-(4-hydroxymethylbenzylamino)propoxycarbonyl)-N-(2-norbornyl)aminoacetic acid;

N-(N'-(2-(2-(2-hydroxymethylphenoxy)benzyl)aminoethoxycarbonyl)-N'-(2-(4-hydroxymethylbenzylamino)propoxycarbonyl)-N-(2-adamantyl)aminoacetic acid;

N-(N'-(2-(2-(2-hydroxymethylphenoxy)benzyl)aminoethoxycarbonyl)-N'-(2-(4-hydroxymethylbenzylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(3-hydroxybenzylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(3-hydroxybenzylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(3-hydroxybenzylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(2-hydroxybenzylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(2-hydroxybenzylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(2-hydroxybenzylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-hydroxyphenethylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(4-hydroxyphenethylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(4-hydroxyphenethylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(3-hydroxyphenethylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(3-hydroxyphenethylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(3-hydroxyphenethylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(2-hydroxyphenethylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(2-hydroxyphenethylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(2-hydroxyphenethylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-dimethylaminobenzylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(4-dimethylaminobenzylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(4-dimethylaminobenzylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-nitrophenethylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(4-nitrophenethylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(4-nitrophenethylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-nitrobenzylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(4-nitrobenzylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(4-nitrobenzylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-chlorobenzylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(4-chlorobenzylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(4-chlorobenzylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-hydroxymethylbenzylamino)ethoxycarbonyl)-N-(2-norbornyl)aminoacetic acid;

N-(N'-(2-(2-(2-hydroxymethylphenylamino)benzyl)aminoethoxycarbonyl)-N'-(2-(4-hydroxymethylbenzylamino)ethoxycarbonyl)-N-(2-adamantyl)aminoacetic acid;

N-(N'-(2-(2-(2-hydroxymethylphenylamino)benzyl)aminoethoxycarbonyl)-N'-(2-(4-hydroxymethylbenzylamino)ethoxycarbonyl)-N-(2-bicyclooctyl)aminoacetic acid;

N-(N'-(2-(2-(2-hydroxymethylphenylamino)benzyl)aminoethoxycarbonyl)-N'-(2-(3-hydroxybenzylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(3-hydroxybenzylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(3-hydroxybenzylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(2-hydroxybenzylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(2-hydroxybenzylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(2-hydroxybenzylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-hydroxyphenethylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(4-hydroxyphenethylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(4-hydroxyphenethylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(3-hydroxyphenethylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(3-hydroxyphenethylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(3-hydroxyphenethylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(2-hydroxyphenethylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(2-hydroxyphenethylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(2-hydroxyphenethylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-dimethylaminobenzylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(4-dimethylaminobenzylamino)propoxycarbonyl)-N-(2-adamantyl)aminoacetic acid;

N-(N'-(2-2-(2-hydroxymethylphenylamino)benzyl)aminoethoxycarbonyl)-N'-(2-(4-dimethylaminobenzylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-nitrophenethylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(4-nitrophenethylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(4-nitrophenethylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-nitrobenzylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(4-nitrobenzylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(4-nitrobenzylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-chlorobenzylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(4-chlorobenzylamino)propoxycarbonyl)-N-(2-adamantyl)aminoacetic acid;

N-(N'-(2-(2-(2-hydroxymethylphenylamino)benzyl)aminoethoxycarbonyl)-N'-(2-(4-chlorobenzylamino)propoxycarbonyl)-N-(2-bicyclooctyl)aminoacetic acid;

N-(N'-(2-(2-(2-hydroxymethylphenylamino)benzyl)aminoethoxycarbonyl)-N'-(2-(4-hydroxymethylbenzylamino)propoxycarbonyl)-N-(2-norbornyl)aminoacetic acid;

N-(N'-(2-(2-(2-hydroxymethylphenylamino)benzyl)aminoethoxycarbonyl)-N'-(2-(4-hydroxymethylbenzylamino)propoxycarbonyl)-N-(2-adamantyl)aminoacetic acid; and N-(N'-(2-(2-(2-hydroxymethylphenylamino)benzyl)aminoethoxycarbonyl)-N'-(2-(4-hydroxymethylbenzylamino)propoxycarbonyl)-N-(2-bicyclooctyl)aminoacetic acid.

EXAMPLE 2

(Activity In Vitro)

Compounds were screened in vitro using the following assay:

High-affinity ligands for the μ-specific opiate receptor are identified from a diverse peptoid library by testing the pools of compounds in solution-phase radioligand competition assays, and tracing the binding activity to individual compounds by iterative resynthesis and screening of smaller sub-pools.

Rat forebrains are homogenized and washed in 50 mM Tris, pH 7.5 containing 20 mM NaCl, 5 mM EGTA, 2 mM $MgCl_2$, 21 μg/mL aprotinin, 0.5 mg/L leupeptin, 0.7 mg/L pepstatin, 0.2 Mm PMSF. 50 μL of membrane (10 mg/mL protein) are dispensed into 1 mL of 50 mM Tris, pH 7.5, 1 nM [$^3$H]-DAMGO and the peptoid mixture. All assays are performed at 100 nM per peptoid.

Nonspecific binding is determined as [$^3$H]-DAMGO bound in the presence of 1 μM naloxone. Incubation is for 1 hr at room temperature. Unbound radioactivity is removed by rinsing the membranes on Whatman GF/B glass fiber filters. Each filter is washed 3 times with 3 mL of 50 mM Tris, pH 7.5, 4° C. Filters are soaked overnight in 5 mL of Beckman ReadySafe scintillation cocktail and then counted for one minute in a Wallac 1409 liquid scintillation counter. Assays are performed in duplicate.

EXAMPLE 3

(Assay In vivo)

Compounds of the invention are tested in vivo as follows:

Male Swiss (ICR) mice (25–30 g) and male Sprague Dawley albino rats (100–125 g) are housed in groups of 5, and allowed food and water ad libitum until the beginning of the experiment.

A. Mouse stretch test: This procedure is a general, non-specific test for detecting antinociceptive activity in a wide variety of pharmacological agents. Each mouse (n=10) is administered either vehicle or test compound (0.1 mg/Kg to 300 mg/Kg) subcutaneously. After 5 min, dilute acetic acid (0.6%) is injected i.p. (0.25 mL/25 g). Each animal is then observed after an additional 5 min, and the number of abdominal twists/hind leg stretches displayed by each mouse is counted for a 5 min. test period. Percent inhibition of response is calculated from 100× (mean number of stretches in vehicle group—mean number of stretches per mouse)/ (mean number of stretches in vehicle group). The dose of compound causing 50% antinociception (at 95% confidence limits) is calculated by regression analysis.

Oral studies are performed with different mice. Test compound (or vehicle) is administered orally, followed by acetic acid injection 25–55 min after administration.

Antagonism studies are performed by first obtaining a dose-response curve for s.c. morphine and vehicle. Mice are administered test compound s.c., (0.1 mg/Kg to 300 mg/Kg) followed 5 min later by morphine in one of 4 doses s.c. (determined according to standard experimental protocol). Morphine antagonism is demonstrated if the morphine dose-response curve is displaced to the right.

B. Rat Formalin Test: Dilute formalin provides a continuous (tonic) background of pain that may be neurochemically and neurophysiologically different from the transient (phasic) pain associated with hot plate and tail-flick tests.

Rats (n=8) are acclimated to individual Plexiglas observation chambers for at least 1 hr prior to testing. Each animal is then injected with 5% formalin (50 μL) or saline (50 μL) s.c. into the dorsal surface of the right hind paw. The rats display two spontaneous behaviors indicative of pain: flinching/shaking of the paw and/or hindquarters, and licking or biting of the injected paw. Flinching is the most reliable behavior to score in rats. The behavior is monitored between 0–10 min (early/acute phase) and 20–35 min (late/tonic phase) following injection.

Four doses of test compound are injected s.c. (0.1 mg/Kg to 300 mg/Kg). The pretreatment time is chosen so that peak antinociceptive activity coincides with the late/tonic phase of response. Results are expressed as mean % antagonism of formalin-induced flinching, and are calculated for individual, drug-treated formalin-injected rats.

C. Neuroadaptation of Rats: This protocol provides information on how rats react to multiple doses of test compounds, and on eventual challenge with naloxone, a standard antagonist of opioid receptors.

Four groups of 6 rats are injected s.c. with either vehicle or test compound at 8:00 AM, 4:00 PM, and midnight over 5 days. On the fifth day, only the morning injection is administered. The initial dosages are: day 1=1 mg/Kg, day 2=2 mg/Kg, days 3–5=4 mg/Kg. Naloxone (3 mg/Kg, s.c.) or saline is administered 4 hr after the final injection of test compound.

On day 4, the rats are acclimated to Plexiglas observation cages in a constant temperature room (20° C.). The animals are trained to have their weights and rectal temperature taken. On day 5, this procedure is repeated before noting baseline readings, and challenging with naloxone or saline. Behaviors are monitored for 30 min before and after challenge with naloxone or saline. After the final weighing and temperature reading, 1 hr post challenge, each animal is euthanized with solid $CO_2$.

Behavioral changes in the 4 groups of rats (vehicle-saline, vehicle-naloxone, compound-naloxone, compound-saline) are assessed by a point-scoring technique (with weighted signs): Cowan et al., *J Pharmacol Exp Ther* (1988) 246:950.

What is claimed is:

1. A compound of Formula 1 which binds to the opioid receptor:

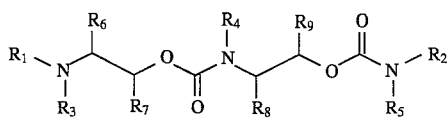

wherein $R_1$ is a group of the formula

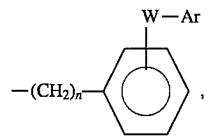

where W is $-(CH_2)_a-$ (where a is 0, 1, or 2), $-O-$, $-NH-$, $-S-$, $-SO-$, or $-SO_2-$, and Ar is phenyl, phenyl-alkyl, phenyl substituted with 1–3 halo, nitro, lower alkyl, hydroxy, amino, alkylamino, dialkylamino, and/or hydroxy-lower alkyl groups, and n is 0, 1, 2, 3, or 4;

$R_2$ and $R_3$ are each independently H, lower alkyl, or

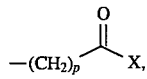

where X is H, OH, lower alkyl, or lower alkoxy, and p is 0, 1, 2, or 3;

$R_4$ is

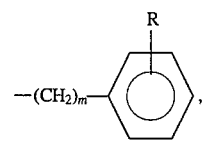

where m is 0, 1, 2, or 3, and R is 1–3 halo, nitro lower alkyl, hydroxy, amino, alkylamino, dialkylamino, and/or hydroxy-lower alkyl groups;

$R_5$ is cycloalkyl, bicycloalkyl, or tricycloalkyl;

$R_6$, $R_7$, $R_8$, and $R_9$ are each independently H or lower alkyl.

2. The compound of claim 1, wherein $R_3$, $R_6$, $R_7$, $R_8$, and $R_9$ are all H.

3. The compound of claim 2, wherein $R_1$ is 2-(2-hydroxymethylphenylthio)benzyl.

4. The compound of claim 3, wherein $R_4$ is 4-hydroxybenzyl.

5. The compound of claim 4, wherein $R_5$ is norbornyl.

6. The compound N-(N'-(2-(2-(2-hydroxymethylphenoxy)benzyl)aminoethoxycarbonyl)-N'-(4-hydroxybenzylaminoethoxy-carbonyl)-N-(2-norbornyl)aminoacetic acid.

* * * * *